(12) United States Patent
Huang et al.

(10) Patent No.: US 9,179,675 B2
(45) Date of Patent: Nov. 10, 2015

(54) USE OF SARMENTINE AND ITS ANALOGS FOR CONTROLLING PLANT PESTS

(71) Applicant: Marrone Bio Innovations, Inc., Davis, CA (US)

(72) Inventors: Huazhang Huang, Durham, NC (US); Ratnakar Asolkar, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 0 days.

(21) Appl. No.: 14/587,929

(22) Filed: Dec. 31, 2014

(65) Prior Publication Data
US 2015/0111749 A1    Apr. 23, 2015

Related U.S. Application Data

(63) Continuation of application No. 13/919,019, filed on Jun. 17, 2013, now Pat. No. 8,957,000, which is a continuation of application No. 12/840,106, filed on Jul. 20, 2010, now Pat. No. 8,466,192.

(60) Provisional application No. 61/227,412, filed on Jul. 21, 2009.

(51) Int. Cl.
| | |
|---|---|
| *A01N 37/02* | (2006.01) |
| *A01N 37/06* | (2006.01) |
| *A01N 37/10* | (2006.01) |
| *A01N 37/18* | (2006.01) |
| *A01N 43/36* | (2006.01) |
| *A01N 43/40* | (2006.01) |
| *A01N 43/46* | (2006.01) |
| *C07C 233/05* | (2006.01) |
| *C07C 233/06* | (2006.01) |
| *C07C 233/11* | (2006.01) |
| *C07D 295/185* | (2006.01) |
| *C07C 57/42* | (2006.01) |
| *C07D 207/06* | (2006.01) |
| *C07D 211/16* | (2006.01) |
| *C07D 233/04* | (2006.01) |
| *C11B 1/00* | (2006.01) |
| *C07C 57/44* | (2006.01) |
| *C07C 69/587* | (2006.01) |
| *C07C 233/08* | (2006.01) |

(52) U.S. Cl.
CPC ............... *A01N 43/36* (2013.01); *A01N 37/02* (2013.01); *A01N 37/06* (2013.01); *A01N 37/10* (2013.01); *A01N 37/18* (2013.01); *A01N 43/40* (2013.01); *A01N 43/46* (2013.01); *C07C 57/42* (2013.01); *C07C 57/44* (2013.01); *C07C 69/587* (2013.01); *C07C 233/05* (2013.01); *C07C 233/06* (2013.01); *C07C 233/08* (2013.01); *C07C 233/11* (2013.01); *C07D 207/06* (2013.01); *C07D 211/16* (2013.01); *C07D 233/04* (2013.01); *C07D 295/185* (2013.01); *C11B 1/00* (2013.01); *C07C 2101/08* (2013.01)

(58) Field of Classification Search
CPC ....... A01N 37/02; A01N 37/06; A01N 37/10; A01N 37/18; A01N 43/36; A01N 43/40; A01N 43/46
See application file for complete search history.

(56) References Cited

U.S. PATENT DOCUMENTS

| | | |
|---|---|---|
| 3,147,261 A | 9/1964 | Mod |
| 4,453,975 A | 6/1984 | Takematsu et al. |
| 4,716,060 A | 12/1987 | Rajadhyaksha et al. |
| 4,902,334 A | 2/1990 | Azuma et al. |
| 5,665,681 A | 9/1997 | Seckinger et al. |
| 6,825,216 B1 | 11/2004 | Trail et al. |
| 2008/0153708 A1 | 6/2008 | Jones |
| 2008/0242740 A1 | 10/2008 | Ley et al. |
| 2008/0317923 A1 | 12/2008 | Ley et al. |
| 2009/0124701 A1 | 5/2009 | Langer et al. |

FOREIGN PATENT DOCUMENTS

| | | |
|---|---|---|
| DE | 225325 A1 | 7/1985 |
| EP | 0577914 A1 | 1/1994 |
| EP | 1520850 A2 | 4/2005 |
| EP | 2058297 A1 | 5/2009 |
| GB | 2247621 A | 3/1992 |
| JP | 04-073954 | 3/1992 |
| JP | 08-268954 | 10/1996 |
| WO | WO 87/04593 A1 | 8/1987 |
| WO | WO 89/031718 A1 | 4/1989 |
| WO | WO 95/15685 A1 | 6/1995 |
| WO | WO 2007104669 A2 | 9/2007 |
| WO | WO 2008065451 | 6/2008 |
| WO | WO 2008135093 A1 | 11/2008 |
| WO | WO 2010078452 A2 | 7/2010 |

OTHER PUBLICATIONS

Alexander, J. P. et al. "The Putative Endocannabinoid Transport Blocker Previous Termly2183240 Next Term is a Potent Inhibitor of Previous Term FAAH Next Term and Several other Brain Serine Hydrolases", J. Am. Chem. Soc. 128, 9699-9704. 2006.
Abarbri et al. "A Synthetic Approach to Natural Dienamides of Insecticidal Interested". Syntheti Communications. 28. 239-249. 1998.
Askolar, R. et al. "Daryamides A-C, Weakly Cytotoxic Polyketides form a Marine-Derived Actinomycete of the Genus *Streptomyces* Strain CNQ-085", J. Nat. Prod. 69, 1756-1759. 2006.

(Continued)

Primary Examiner — Valerie Rodriguez-Gracia
(74) Attorney, Agent, or Firm — Chainey P. Singleton; Daniel J. Chalker; Chalker Flores, LLP

(57) ABSTRACT

Methods and compositions for controlling plant pests, particularly weeds and/or plant phytopathogens using sarmentine and/or analogs thereof are disclosed.

7 Claims, No Drawings

(56) References Cited

OTHER PUBLICATIONS

Batish, D. R. et al. "Phytotoxicity of Lemon-Scented Eucalypt Oil and its Potential use as a Bioherbicide", Crop Protection 23, 1209-1214. 2004.
Bednarek et al. "Novel Polymers Based on Atom Transfer Radical Polymerization of 2 Methoxyethyl Acrylate". Journal of Polymer Science. 45. 333-340. 2006.
Bertin, C. et al. "Grass Roots Chemistry: Meta-Tyrosine, an Herbicidal onprotein amino acid" Proc. Nat'l. Acad. Sci. USA 104, 16964-16969. 2007.
Carter, P. et al. "Probing the Mechanism and Improving the Rate of Substrate-Assisted Catalysis in Subtilisin BPN'", Biochem. 30, 6142-6148. 1991.
Cho, J. et al. "Lucentamycins A-D, Cytotoxic Peptides from the Marine-Derived Actinomycete Nocardiopsis Lucentensis", J. Nat. Prod. 70, 1321-1328. 2007.
Choi, E.M. et al. "Investigations of Anti-Inflammatory and Antinociceptive Activities of Piper Cubeba, Physalis 20 Angulata and Rosa Hybrid", J. Ethanopharmacol. 89, 171-175. 2003.
Corey, D. et al. "An investigation into the Minimum Requirements for Peptide Hydrolysis by Mutation of the Catalytic Triad of Trypsin", J. Am. Chem. Soc. 114, 1784-1790. 1992.
Cornacchione, S. et al. "In Vivo Skin Antioxidant Effect of a New Combination Based on a specific Vitis vinifera Shoots 20 Extract and a Biotechnological Extract". J. Drugs in Dermatol. 6S, 8-13. 2007.
Das, B. et al. "Alkamides and other Constituents of Piper Longum", Planta Med 62, 582. 1996.
Database CA [Online] Chemical Abstracts Service, Columbus, Ohio, US: XP002687722, retrieved from STN Database Accession No. 1981:514761.
Duke, S. O.et al. "Chemicals from nature for weed management". Weed Sci. 50, 138-151. 2002.
Elias, Dana D. et al. "Especies Vegetales Invasoras en Andalucia", Junte de Andalucia, Consejeria de Medio Ambiente. 2005.
Ghoshal, S. et al. "Antiamoebic Activity of Piper Longum Fruits Against Entamoeba Histolytica in Vitro and in Vivo", J. Ethanopharmacol. 50, 167-170. 1996.
Fukuda, M.; et al. "Phytotoxic Activity of Middle-Chain Fatty Acids I: Effects on Cell Constituents", Pest. Biochem. Physiol., 80, 143-150. 2004.
Gianessi, L. et al. "The Value of Herbicides in U.S. Crop Production", Weed Technol 21, 559-566. 2007.
Kiuchi, F. et al. "Studies on Crude Drugs Effective on Visceral Larva Migrans. IV. Isolation and Identification of Larvicidal Principles in Pepper", Chemical and Pharmaceutical Bulletin 36, 2452-2465. 1998.
Krishnamurthi, A. The Wealth of India Raw Materials, vol. 8. CSIR, New Delhi, India, p. 96. 1969.
Lederer, B. et al. "Phytotoxic Activity of Middle-Chain Fatty Acids II: Peroxidation and Membrane Effects", Pest. Biochem. Physiol. 80. 151-156. 2004.
Li, C.Y. et al. "Isolation and Identification of Antiplatelet Aggregatory Principles from the Leaves of Piper lolot", J. Agric. Food Chem. 55, 9436-9442. 2007.
Likhitwitayawuid, K. et al. "Structural Elucidation and Synthesis of New Components Isolated from Piper Samentosum", Tetrahedron 43, 3689-3694. 1987.
Macias, F. A. et al. "Allelopathy—a Natural Alternative for Weed Control", Pest Manag Sci., 63, 327-348. 2007.
Mata, R. et al. "Antimycobacterial Compounds from Piper Sanctum", J. Nat. Prod. 67, 1961-1968. 2004.
Nalina et al. "The Crude Aqueous Extract of Piper Betle L. and Its Antibacterial Effect Towards *Streptococcus mutans*". American Journal of Biotechnology and Biochemistry. 3, 10-15. 2007.
Parma, V. et al. "Phytochemistry of the Genus *Piper*", Phytochem. 46, 597-673. 1997.
Parma, V. et al. "Polyphenols and Alkaloids from *Piper* Species Phytochem" 49. 1069-1078. 1998.
Rukachaisirikul, T. et al. "Chemical Constituents and Bioactivity of Piper Sarmentosum" J. Ethnopharmacol. 93, 173-176. 2004.
Solomon, G. M.et al. "Environment and Health: 6. Endocrine Disruption and Potential Human Health Implications", Can Med Assoc J 163, 1471-1476. 2000.
Stillerman, K. et al. "Environmental Exposures and Adverse Pregnancy Outcomes: A Review of the Science" Reproductive Sci. 15, 631-650. 2008.
Toshiake, M. et al. "Germination and growth inhibition of acylnornicotines from section repandae of the genus *Nicotiana* and synthetic acylnornicotines:" Acgricultural and Biological Chemistry 52. 1899-1903. 19883.
Tuntiwachwuttikul, P. et al. "Chemical Constituents of the Roots of Piper Sarmentosum", Chem. Pharm. Bull. 54, 149-151. 2006.
Vedhanayaki, G. et al. "Analgesic Activity of Piper Longum Linn. Root", Ind. J. Exp. Biol. 41, 649-651. 2003.
Whaley, C. M. et al. "A New Mutation in Plant ALS Confers Resistance to Five Classes of ALS-inhibiting Herbicides", Weed Sci. 55, 83-90. 2007.
Yang, Y. C. et al. "A Piperidine Amide Extracted from Piper Longum L. Fruit Shows Activity Against Aedes Aegypti Mosquito Larvae", J. Agric. Food Chem. 50, 3765- 3767. 2002.
International Search Report and Written Opinion based on PCT/US2010/042607 dated Feb. 23, 2011.
Examination Report for New Zealand Application No. 298271 dated Oct. 18, 2012.
Extended European Search Report for European Application No. 10802779.8 dated May 12, 2012.
Partial European Search Report for European Application No. 13193523 dated Feb. 4, 2014.

USE OF SARMENTINE AND ITS ANALOGS FOR CONTROLLING PLANT PESTS

FIELD OF THE INVENTION

This invention relates to compositions and methods for controlling plant pests, particularly weeds and/or plant phytopathogens such as plant pathogenic bacteria, viruses, fungi, nematodes, and insects using sarmentine or analogs thereof as an active ingredient.

BACKGROUND OF THE INVENTION

Utilization of synthetic herbicides not only prevents economic loss in food production, but also improves quality of crop products (Gianessi, L. P.; Reigner, N. P. The value of herbicides in U.S. crop production, Weed Technol. 2007, 21, 559-566). However, the use of synthetic herbicides may cause side-effects on environment and human health (Solomon, G. M.; and Schettler, T. Environment and health: 6. Endocrine disruption and potential human health implications, CMAJ, 2000, 163, 1471-1476; Stillerman, K. P.; Mattison, D. R.; Giudice, L. C.; Woodruff, T. J. Environmental exposures and adverse pregnancy outcomes: A review of the science. Reproductive Sci. 2008, 15, 631-650.) except that it also leads to an increasing resistance among many weed species (Whaley, C. M.; Wilson, H. P.; Westwood, J. H. A new mutation in plant ALS confers resistance to five classes of ALS-inhibiting herbicides, Weed Sci. 2007, 55, 83-90.). Therefore, it is very necessary to develop alternative means for weed management that are eco-friendly, cost-effective and bio-efficacious (Duke, S. O.; Dayan, F. E.; Rimando, A. M.; Schrader, K. K.; Aliotta, G.; Oliva, A.; Romagni, J. G. Chemicals from nature for weed management. Weed Sci. 2002, 50, 138-151).

The use of natural phytochemicals is one of these alternative means (Batish, D. R.; Setia, N.; Singh, H. P.; Kohli, R. K. Phytotoxicity of lemon-scented eucalypt oil and its potential use as a bioherbicide, Crop Protection, 2004, 23, 1209-1214). Due to allelopathic properties, many of these chemicals are either released in air or soil to kill neighboring weeds or to inhibit their germination and/or growth. These phytotoxic chemicals include phenolic compounds (e.g., catechin, ellagic acid, sorgoleone, juglone, ceratiolin, usnic acid), terpenoids (e.g., 1,8-cineole, geranial, neral, cinmethylin, solstitiolide), quassinoids (e.g., ailanthone, chaparrine, ailanthinol B), benzoxazinoids (e.g., hydroxamic acids), glucoinolates (e.g., glucohirsutin, hirsutin, arabin), and some amino acids such as meta-tyrosine (Macias, F. A.; Molinillo, J. M. G.; Varela, R. M.; Galindo, J. C. J. Allelopathy—a natural alternative for weed control. Pest Manag Sci., 2007, 63, 327-348; Bertin, C.; Weston, L. A.; Huang, T.; Jander, G.; Owens, T.; Meinwald, J.; Schroeder, F. C. Grass roots chemistry: meta-Tyrosine, an herbicidal nonprotein amino acid. PNAS, 2007, 104, 16964-16969). Commercially available herbicides include products based on clove oil, lemongrass oil and d-limonene.

The Genus Piper

The genus Piper in the Piperaceae family contains approximately 2000 species found primarily in tropical regions. Plants of this genus are normally slender aromatic climbers with perennial woody roots. The fruits commonly known as "pippali" in India and "Bi Bo" in China are used as a spice and also as a preservative in pickles. They are also used as cattle feed.

In traditional medicinal practice, P. longum fruits have been advocated to be beneficial in treatment of diseases such as gonorrhea, menstrual pain, tuberculosis, sleeping problems, respiratory tract infections, chronic gut-related pain, and arthritic conditions (Krishnamurthi, A. 1969. The Wealth of India Raw Materials, vol. 8. CSIR, New Delhi, India, p. 96; Ghoshal, S.; Prasad, B. N. K.; Lakshmi, V. Antiamoebic activity of Piper longum fruits against Entamoeba histolytica in vitro and in vivo, J. Ethanopharmacol. 1996, 50, 167-170; Choi, E. M.; Hwang, J. K. Investigations of anti-inflammatory and antinociceptive activities of Piper cubeba, Physalis angulata and Rosa hybrid, J. Ethanopharmacol. 2003, 89, 171-175, Mata, R.; Morales, I.; Perez, O.; Rivero-Cruz, I.; Acevedo, L.; Enriquez-Mendoza, I.; Bye, R.; Franzblau, S.; Timmermann, B. Antimycobacterial compounds from Piper sanctum, J. Nat. Prod. 2004, 67, 1961-1968). Other reported beneficial effects of P. longum include analgesic and diuretic effects, relaxation of muscle tension, and alleviation of anxiety (Vedhanayaki, G.; Shastri, G. V.; Kuruvilla, A. Analgesic activity of Piper longum Linn. Root, Ind. J. Exp. Biol. 2003, 41, 649-651; Das, Biswanath, D.; Kashinatham, A.; Srinivas, K. V. N. S. Alkamides and other constituents of Piper longum, Planta Med, 1996, 62, 582). In addition, pipernonaline from P. longum has been found to possess mosquito larvicidal activity (Yang, Y. C.; Lee, S. G.; Lee, H. K.; Kim, M. K.; Lee, S. H.; Lee, H. S. A piperidine amide extracted from Piper longum L. fruit shows activity against Aedes aegypti Mosquito Larvae, J. Agric. Food Chem., 2002, 50, 3765-3767).

An alkaloid has been isolated from Piper nigrum (pepper) which is an alkenylene piperidine amide containing a C18 alkenylene with two or more double bonds. This compound has been found to inhibit mycotoxin biosynthesis. (U.S. Pat. No. 6,825,216).

Sarmentine

N-(2E,4E-Decadienoyl) pyrrolidine (also called sarmentine) was originally separated from the fruit of Piper sarmentosum in 1987 [Likhitwitayawuid, K., Ruangrungsi, N, Lange, G and Decicco, C., Structural Elucidation and Synthesis of New Components isolated from Piper Samentosum, Tetrahedron 1987 (43) 3689-3694] and also from Piper nigrum in 1988 [Kiuchi, F., Nakamura, N., Tsuda, Y., Kondo, K and Yoshimura, H. Studies on Crude Drugs Effective on Visceral Larva Migrans. IV. Isolation and Identification of Larvicidal Principles in Pepper Chemical and Pharmaceutical Bulletin 1988(36):2452], and first synthesized in 1995 [Bernabeu, M., Chinchilla, R. and Najera, C., (2E,4E)-5-Tosyl-2,4-pentadienamides: New Dienic Sulfones for the Stereoselective Synthesis of (2E,4E)-Dienamides, Tetrahedron Letter, 1995 (36)3901-3904]. Sarmentine has been found to be in vivo skin antioxidant protecting photoaged skin [Cornacchione, S.; Sadick, N. S.; Neveu, M.; Talbourdet, S.; Lazou, K.; Viron, C.; Renimel, I.; de Quéral, D.; Kurfurst, R.; Schnebert, S.; Heusèle, C.; André, P.; Perrier E. In vivo skin antioxidant effect of a new combination based on a specific Vitis vinifera shoots extract and a biotechnological extract. J. Drugs in Dermatol. 2007, 6S, 8-13], display antiplatelet aggregation activity [Li, C. Y.; Tsai, W.; Damu, A. G.; Lee, E. J.; Wu, T. S.; Dung. N. X.; Thang, T. D.; Thanh, L. Isolation and identification of antiplatelet aggregatory principles from the leaves of Piper lolot, J. Agric. Food Chem. 2007, 55, 9436-9442], antiplasmodial and antimycobacterial activities [Tuntiwachwuttikul, P.; Phansa, P.; Pootaeng-on, Y.; Taylor, W. C. Chemical constituents of the roots of Piper Sarmentosum, Chem. Pharm. Bull. 2006, 54, 149-151] and antituberculosis activity [Rukachaisirikul, T.; Siriwattanakit, P.; Sukcharoenphol, K.; Wongvein, C.; Ruttanaweang, P.; Wongwattanavuch, P.; Suksamrarn, A. Chemical constituents and bioactivity of Piper sarmentosum, J. Ethnopharmacol., 2004, 93, 173-176]. Sarmentine is used as a solubilizer of hydrophobic compounds in cosmetics and pharmaceuticals (Stephen, T.; Andrew, H. Compositions comprising macromolecular assembles of lipid surfactant, PCT Publication No. WO/2008/065451).

BRIEF SUMMARY OF THE INVENTION

The invention is directed to compositions comprising sarmentine and/or its analogs for use against plant pests, particularly plant phytopathogens such as plant pathogenic bacteria, fungi, insects, nematodes and/or as a pre- and post-emergence herbicide against weeds, as well as the use of sarmentine and/or its analogs in formulating such pesticidal (phytopathogenic or herbicidal composition). In a particular embodiment, the sarmentine analog(s) which may be used in compositions and methods of the present invention has substantially the same activity as sarmentine. As defined herein "substantially the same activity as sarmentine" means that it has at least about 80% of the phytopathogenic and/or herbicidal activity of sarmentine and preferably at least about 90% of the phytopathogenic and/or herbicidal activity of sarmentine and even more preferably at least about 95% of the phytopathogenic and/or herbicidal activity of sarmentine.

The sarmentine analogs includes but is not limited to: N-(Decanoyl)pyrrolidine, N-(Decenoyl)pyrrolidine, N-(Decanoyl)piperidine, N-(trans-Cinnamoyl)pyrrolidine, (2E,4Z-Decadienoyl)pyrrolidine, N-(Decenoyl)piperidine, (2E,4Z-Decadienoyl)piperidine, (2E,4Z-Decadienoyl)hexamethleneimine, N-(Decenoyl)hexamethyleneimine, N-(Decanoyl)hexamethyleneimine, decanoic acid, 2E-Decenoic acid.

In a particular embodiment, the invention is directed to a an isolated sarmentine analog having the structure:

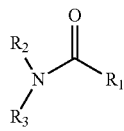

Where R1 is an alkyl, alkenyl, alkynyl, heterocyclyl, aromatic, aryl group, NH-substituted, or N,N-substituted group, the length of R1 chain can be from 4 to 20 atoms, the preferred length will be from 6 to 12 atoms;
Wherein R2 and R3 are alkyl, alkenyl, alkynyl, cycloalkyl, cycloalkenyl, aromatic, arylalkyl, heterocyclyl or heteroaryl or R2+R3+N can be an N-containing heterocyclic or herteroaryl ring consisting of between 3-18 atoms and preferably between 5 to 8 atoms.

In a more particular embodiment, the isolated samentine analog includes but is not limited to: (2E,4Z-Decadienoyl) pyrrolidine; (2E,4Z-Decadienoyl)hexamethleneimine and N-(Decenoyl)hexamethyleneimine.

The compositions of the present invention may further comprise one or more other herbicides or phytopathogenic modulating agents. The invention is also directed to uses of one or more sarmentine and/or its analogs for preparation of a composition for use as a pre or post emergent herbicide and/or as an anti-phytopathogenic agent.

In a particular embodiment, the invention is directed to a method for modulating phytopathogenic infection in a plant comprising applying to the plant and/or seeds thereof and/or substrate used for growing said plant an amount of a sarmentine and/or its analogs effective to modulate said phytopathogenic infection. The substrate for growing said plant in a particular embodiment may include but is not limited to soil, an artificial growth substrate, water or sediment.

In another particular embodiment, the invention is directed to a method for modulating emergence of monocotyledonous, or dicotyledonous weeds in a substrate comprising applying to the weeds and/or substrate an amount of a sarmentine and/or its analogs effective to modulate emergence of monocotyledonous or dicotyledonous weeds in the substrate. The substrate may include but is not limited to soil, an artificial growth substrate (e.g., rice growing system), water or sediment. The sarmentine and/or its analogs is applied to the substrate prior to emergence of said weed. Alternatively, the sarmentine and/or its analogs may be applied to the substrate and/or weed after emergence of said weed(s).

The weeds may be broadleaved and/or grass weeds. In a particular embodiment, the weeds are in a rice growing system and the weed is a rice weed(s).

In a particular embodiment, the sarmentine and/or its analogs is applied in an amount of about 0.005 mg/ml to about 20 mg/ml. In a more particular embodiment, the sarmentine and/or its analogs is applied in an amount of about 0.01 to about 15 mg/ml. In yet a more particular embodiment, the sarmentine and/or its analogs is applied in an amount of about 0.1 to about 10 mg/ml.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, the term "modulate" is used to mean to alter the amount of phytopathogenic infection or rate of spread of phytopathogenic infection.

Sarmentine and its Analogs

The sarmentine and/or its analogs used in the method of the present invention may have the following structure:

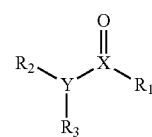

Where X includes but is not limited to sulfur, phosphorus, boron or carbon; Y includes but is not limited to carbon, oxygen, nitrogen, sulfur, boron or phosphorous; $R_1$ includes but is not limited to hydrogen, hydroxyl, halogen, alkyl, alkoxy, alkenyl, alkynyl, cycloalkyl, cycloalkenyl, aromatic, arylalkyl, heterocyclyl and heteroaryl; $R_2$ includes but is not limited to hydrogen, hydroxyl, halogen, alkyl, alkoxy, alkenyl, alkynyl, cycloalkyl, aromatic, arylalkyl, heterocyclyl and heteroaryl; $R_3$ includes but is not limited to hydrogen, hydroxyl, halogen, alkyl, alkoxy, alkenyl, alkynyl, cycloalkyl, aromatic, arylalkyl, heterocyclyl and heteroaryl; wherein $R_2+R_3+Y$ can be a cyclic or heterocyclyl ring containing 4-50 atoms. Each of these is optionally substituted.

As used herein, the term "alkyl" refers to a saturated hydrocarbon radical which may be straight-chain or branched-chain (e.g., ethyl, isopropyl, t-amyl, or 2,5-dimethylhexyl, etc.). This definition applies both when the term is used alone and when it is used as part of a compound term.

The terms "cycloalkyl" and "cycloalkenyl" refer to a saturated hydrocarbon ring and includes bicyclic and polycyclic rings. Similarly, cycloalkyl and cycloalkenyl groups having a heteroatom (e.g., N, O, or S) in place of a carbon ring atom may be referred to as "heterocycloalkyl", "heterocyclyl," and "heterocycloalkylene," respectively.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy, aryloxy, and t-butoxy).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g., N, O, or S) in place of a carbon ring atom are referred to as "heteroaryl."

The terms "arylalkyl," "arylalkenyl," and "aryloxyalkyl" refer to an aryl radical attached directly to an alkyl group, an alkenyl group, or an oxygen atom which is attached to an alkyl group, respectively. For brevity, aryl as part of a combined term as above is meant to include heteroaryl as well.

The term "halo" or "halogen," by itself or as part of another substituent, means, unless otherwise stated, a fluorine, chlorine, bromine, or iodine atom. Additionally, terms such as "haloalkyl" are meant to include monohaloalkyl and polyhaloalkyl.

The term "hetero" as used in a "heteroatom-containing alkyl group" (i.e., a "heteroalkyl" group) or a "heteroatom-containing aryl group" (i.e., a "heteroaryl" group) refers to a molecule, linkage, or substituent in which one or more carbon atoms are replaced with an atom other than carbon, e.g., nitrogen, oxygen, sulfur, phosphorus, or silicon.

In one particular embodiment, the sarmentine analog has the following structure:

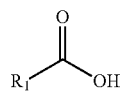

Where $R_1$ is an alkyl, alkenyl, alkynyl, herterocyclyl, aromatic, aryl group, NH-substituted, or N,N-substituted group. In a specific embodiment, $R_1$ is an alkyl or alkenyl moiety containing from 4 to 20 atoms and preferably from 6 to 12 atoms. In a more specific embodiment, $R_1$ is a $C_{5-15}$ alkyl or $C_{5-15}$ alkenyl group. In yet a very specific embodiment, $R_1$ is a $C_{6-12}$ alkyl or $C_{6-12}$ alkenyl group. Possible alkenyl include but are not limited to linear alkenyl fatty acids, branched alkenyl fatty acids, cycloalkenyl substituted fatty acids (e.g., cyclohexenylpropanoic acid, cyclohexenylbutanoic acid, cyclohexenylpentanoic acid and so on), heterocycloalkenyl (e.g., 4-[1,2,3,4-tetrahydropyridinyl]butanoic acid).

In another particular embodiment, the sarmentine analog has the following structure:

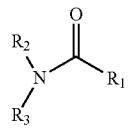

Where R1 is an alkyl, alkenyl, alkynyl, herterocyclyl, aromatic, aryl group, NH-substituted, or N,N-substituted group, the length of $R_1$ chain can be from 4 to 20 atoms, the preferred length will be from 6 to 12 atoms.

Wherein $R_2$ and $R_3$ are alkyl, alkenyl, alkynyl, cycloalkyl, cycloalkenyl, aromatic, arylalkyl, heterocyclyl or heteroaryl; or alternatively $R_2+R_3+N$ can be an N-containing heterocyclic moiety.

One of skill in the art will appreciate that any sarmentine derivatives-containing materials for weed or phytopathogen management is included. Sarmentine derivatives in these materials can be natural and/or synthesized.

In certain embodiments, natural sarmentine derivatives may be obtained from plants, fungi, bacteria and soils. In a particular embodiment, sarmentine and its analogs used in the method of the present invention may be obtained from the fruits, leaves, stems and roots of any *Piper* species. In a more particular embodiment, non-limiting examples of *Piper* species that may contain sarmentine derivatives include but are not limited to the following species such as *Piper aborescens, P. acutisleginum, P. aduncum, P. amalago, P. argyrophylum, P. attenuatum, P. auranticaum, P. austrosinense* T., *P. arboricola* C. DC., *P. banksii, P. bartlingianum, P. betle* L., *P. boehmeriifolium* var. *tonkinense* C. DC., *P. brachystachyum, P. callosum, P. chaba, P. chiadoense, P. cubeba* L., *P. damiaoshaneense, P. demeraranum, P. falconeri, P. futokadsura, P. guayranum, P. guineense, P. hainanense* Hemsl. in F. B. Forbes and Hemsl., *P. hamiltonii, P. hancei* Maxim., *P. khasiana, P. kadsura* (Choisy) Ohwi, *P. laetispicum* C. DC., *P. longum* L., *P. longum* var. ("round peepal"), *P. macropodum, P. manii, P. martinii* C. DC., *P. methysticum, P. nepalense, P. novae hollandiae, P. nigrum* L., *P. nudibaccatum* Y. C. Tseng, *P. officinarum, P. peepuloides, P. pedicellosum, P. ponesheense* C. DC., *P. puberulilimbum* C. DC., *P. puberulum* (Benth.) Maxim., *P. pubicatulum* C. DC., *P. ridleyi, P. rugosum, P. retrofractum* Vahl, *P. ribesioides, P. sanctum, P. sarmentosum* R., *P. schmidtii, P. semiimmersum* C. DC., *P. sintenense, P. spirei* C. DC., *P. syvaticum, P. thomsoni, P. verruscosum, P. trichostachyon, P. wallichii* (Miq.), *P. wightii* [Parma, V., Jain, S., Bisht, K., Jain, R., Poonam, T., Jha, A., Tyagi, O., Prasad, A., Wengel, J., Olsen, C. and Boll., P., Phytochemistry of the Genus *Piper*, Phytochem. 1997 (46) 597-673; Parma, V., Jain, S., Gupta, S., Talwar, S., Rajwanshi, V., Kumar, R., Azim, A., Malhotra, S., Kumar, N., Jain, R., Sharma, N., Tyagi, O., Lawrie, S., Errington, W., Howarth, O., Olsen, C., Singh, S. and Wengel, J. Polyphenols and Alkaloids from *Piper Species* Phytochem. 1998 (49) 1069-1078]. Sarmentine derivatives may also be obtained from microorganisms such as Actinomycetes [Cho, J., Williams, P., Kwon, H., Jensen, P., and Fenical, W., Lucentamycins A-D, Cytotoxic Peptides form the Marine-Derived Actinomycete *Nocardiopsis lucentensis, J. Nat. Prod.,* 2007 (70) 1321-1328; Askolar, R., Jensen, P., Kauffman, C., and Fenical, W., Daryamides A-C, Weakly Cytotoxic Polyketides form a Marine-Derived Actinomycete of the Genus *Streptomyces* Strain CNQ-085, *J. Nat. Prod.,* 2006 (69), 1756-1759].

Sarmentine derivatives can be extracted and purified in any physical and chemical means from *Piper longum* using procedures set forth in the Example, infra, or using procedures known in the art (see, for example, Likhitwitayawuid, K., Ruangrungsi, N, Lange, G and Decicco, C., Structural Elucidation and Synthesis of New Components isolated from *Piper Samentosum Tetrahedron* 1987 (43) 3689-3694 and Kiuchi, F., Nakamura, N., Tsuda, Y., Kondo, K and Yoshimura, H. Studies on Crude Drugs Effective on Visceral Larva Migrans. IV. Isolation and Identification of Larvicidal Principles in Pepper *Chemical and Pharmaceutical Bulletin* 1988(36):24521. They can also be chemically synthesized using for example, the method set forth in [Bernabeu, M., Chinchilla, R. and Najera, C., (2E,4E)-5-Tosyl-2,4-pentadienamides: New Dienic Sulfones for the Stereoselective Synthesis of (2E,4E)-Dienamides, *Tetrahedron Letter,* 1995 (36) 3901-]]. In a particular embodiment, a *Piper longum* sample is subject to extraction with an alkyl alcohol, preferably methanol. Sarmentine is subsequently isolated from the extract by for example, column chromatography, more particularly by HPLC and fractions containing the sarmentine are identified by, for example bioassay.

In a particular embodiment, the compound used may be sarmentine, also known as N-(2E,4E-decadienoyl) pyrrolidine. Natural sarmentine can exist in either plant extracts or a purified form. The sarmentine analog may also be N-(Decanoyl)pyrrolidine, N-(Decenoyl)pyrrolidine N-(Decanoyl) piperidine, N-(trans-Cinnamoyl)pyrrolidine, (2E,4Z-Decadienoyl)pyrrolidine N-(Decenoyl)piperidine, (2E,4Z-Decadienoyl)piperidine, (2E,4Z-Decadienoyl) hexamethyleneimine, N-(Decenoyl)hexamethyleneimine, N-(Decanoyl)hexamethyleneimine, Decanoic acid or 2E-Decenoic acid.

Formulations

Sarmentine and/or sarmentine analog-containing herbicidal compositions (also alternatively referred to as "formulations") can be formulated in any form. Non-limiting formulation examples include emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), etc. In any formulation described herein, percent of sarmentine and/or its analogs is within a range of 0.01% to 99.99%. In a particular embodiment, the formulations may be free of surfactants.

The compositions of the invention may further comprise a carrier and/or diluent. The term, 'carrier' as used herein means an inert, organic or inorganic material, with which the active ingredient is mixed or formulated to facilitate its application to the soil, seed, plant or other object to be treated, or its storage, transport and/or handling. Examples of carrier vehicles to be used when applying to growth substrates include, but are not limited to, active charcoal, corn gluten meal, soybean meal, vermiculite, bentonite, kaolinite, wheat germ, almond hulls, cottonseed meal, Fuller's earth, orange pulp, rice hulls, sawdust, Gum arabic, etc. If desired, plant essential oils such as cinnamon, clove, thyme (eugenol as active ingredient), wintergreen, soy methyl ester, citronella and pine oil, citrus oil (1-limonene as active ingredient) and the like, can be included in the granules. As noted above, the active ingredient alone or in the presence of the carrier vehicles, may be dissolved in for example, water, or organic solvent such as ethanol, formic acid or ethanol.

In further embodiments, sarmentine and its analogs themselves are easily oxidized because of two conjugated double bonds. This is proven by the fact that sarmentine can be an in vivo antioxidant for photoaged skin 11 [Cornacchione, S.; Sadick, N. S.; Neveu, M.; Talbourdet, S.; Lazou, K.; Viron, C.; Renimel, I.; de Queral, D.; Kurfurst, R.; Schnebert, S.; Heusele, C.; Andre, P.; Perrier, E., In vivo skin antioxidant effect of a new combination based on a specific *Vitis vinifera* shoot extract and a biotechnological extract, *J. drugs in Dermatol.* 2007 (6 suppl) S8-13]. Therefore, any antioxidant can be added into the sarmentine and/or its analogs-containing formulation to boost and/or elongate the phytotoxic activity. The non-limiting examples of antioxidants include alpha tocopherol, beta carotene, ascorbic acid, zinc oxide, titanium oxide, *Gynostemma pentaphyllum* extract, *Vaccinium angustifolium* (Blueberry) fruit extract, *Pinus strobus* bark extract, rhaponticin, plankton extract, *Monostroma* sp. extract, algae extract, venuceane, rosmarinic acid, and any other plant extracts or antioxidants.

Examples of phytopathogens controlled by sarmentine and/or its analogs in the method of the present invention include but are not limited to plant viruses, phytopathogenic fungi or bacteria, insects or nematodes. In a specific embodiment, the viruses include but are not limited to TMV, tobacco or cucumber mosaic virus, ringspot virus, necrosis virus, maize dwarf mosaic virus. Phytopathogenic fungi include but are not limited to *Fusarium* sp., *Botrytis* sp., *Monilinia* sp., *Colletotrichum* sp., *Verticillium* sp.; *Microphomina* sp., and *Phytophtora* sp., *Mucor* sp., *Rhizoctonia* sp., *Geotrichum* sp., *Phoma* sp., and *Penicillium* sp. Phytopathognic bacteria include but is not limited to *Bacillus* sp. or *Xanthomonas* sp.

Nematodes that may be controlled using the method of the present invention include but are not limited to parasitic nematodes such as root-knot, cyst, and lesion nematodes, including *Heterodera* and *Globodera* sp.; particularly *Globodera rostochiensis* and *G. pailida* (potato cyst nematodes); *Heterodera glycines* (soybean cyst nematode); *H. schachtii* (beet cyst nematode); and *H. avenae* (cereal cyst nematode).

Phytopathogenic insects controlled by the method of the present invention include but are not limited to insects from the order (a) Lepidoptera, for example, *Acleris* sp., *Adoxophyes* sp., *Aegeria* sp., *Agrotis* sp., *Alabama argillaceae, Amylois* sp., *Anticarsia gemmatalis, Archips* sp., *Argyrotaenia* sp., *Autographa* sp., *Busseola fusca, Cadra cautella, Carposina nipponensis, Chilo* sp., *Choristoneura* sp., *Clysia ambiguella, Cnaphalocrocis* sp., *Cnephasia* sp., *Cochylis* sp., *Coleophora* sp., *Crocidolomia binotalis, Cryptophlebia leucotreta, Cydia* sp., *Diatraea* sp., *Diparopsis castanea, Earias* sp., *Ephestia* sp., *Eucosma* sp., *Eupoecilia ambiguella, Euproctis* sp., *Euxoa* sp., *Grapholita* sp., *Hedya nubiferana, Heliothis* sp., *Hellula undalis, Hyphantria cunea, Keiferia lycopersicella, Leucoptera scitella, Lithocollethis* sp., *Lobesia botrana, Lymantria* sp., *Lyonetia* sp., *Malacosoma* sp., *Mamestra brassicae, Manduca sexta, Operophtera* sp., *Ostrinia nubilalis, Pammene* sp., *Pandemis* sp., *Panolis flammea, Pectinophora gossypiella, Phthorimaea operculella, Pieris rapae, Pieris* sp., *Plutella xylostella, Prays* sp., *Scirpophaga* sp., *Sesamia* sp., *Sparganothis* sp., *Spodoptera* sp., *Synanthedon* sp., *Thaumetopoea* sp., *Tortrix* sp., *Trichoplusia ni* and *Yponomeuta* sp.; (b) Coleoptera, for example, *Agriotes* sp., *Anthonomus* sp., *Atomaria linearis, Chaetocnema tibialis, Cosmopolites* sp., *Curculio* sp., *Dermestes* sp., *Diabrotica* sp., *Epilachna* sp., *Eremnus* sp., *Leptinotarsa decemlineata, Lissorhoptrus* sp., *Melolontha* sp., *Orycaephilus* sp., *Otiorhynchus* sp., *Phlyctinus* sp., *Popillia* sp., *Psyl-* liodes sp., *Rhizopertha* sp-, Scarabeidae, *Sitophilus* sp., *Sitotroga* sp., *Tenebrio* sp., *Tribolium* sp. and *Trogoderma* sp.; (c) Orthoptera, for example, *Blatta* sp., *Blattella* sp., *Gryllotalpa* sp., *Leucophaea maderae, Locusta* sp., *Periplaneta* sp. and *Schistocerca* sp.; (d) Isoptera, for example, *Reticulitermes* sp.; (e) Psocoptera, for example, *Liposcelis* sp.; (f) Anoplura, for example, *Haematopinus* sp., *Linognathus* sp., *Pediculus* sp., *Pemphigus* sp. and *Phylloxera* sp.; (g) Mallophaga, for example, *Damalinea* sp. and *Trichodectes* sp.; (h) Thysanoptera, for example, *Frankliniella* sp., *Hercinotnrips* sp., *Taeniothrips* sp., *Thrips palmi, Thrips tabaci* and *Scirtothrips aurantii*; (i) Heteroptera, for example, *Cimex* sp., *Distantiella theobroma, Dysdercus* sp., *Euchistus* sp., *Eurygaster* sp., *Leptocorisa* sp., *Nezara* sp., *Piesma* sp., *Rhodnius* sp., *Sahlbergella singularis, Scotinophara* sp. and *Tniatoma* sp.; (j) Homoptera, for example, *Aleurothrixus floccosus, Aleyrodes brassicae, Aonidiella* sp., Aphididae, *Aphis* sp., *Aspidiotus* sp., *Bemisia tabaci, Ceroplaster* sp., *Chrysomphalus aonidium, Chrysomphalus dictyospermi, Coccus hesperidum, Empoasca* sp., *Eriosoma larigerum, Erythroneura* sp., *Gascardia* sp., *Laodelphax* sp., *Lecanium corni, Lepidosaphes* sp., *Macrosiphus* sp., *Myzus* sp., *Nephotettix* sp., *Nilaparvata* sp., *Paratoria* sp., *Pemphigus* sp., *Planococcus* sp., *Pseudaulacaspis* sp., *Pseudococcus* sp., *Psylla* sp., *Pulvinaria aethiopica, Quadraspidiotus* sp., *Rhopalosiphum* sp., *Saissetia* sp., *Scaphoideus* sp., *Schizaphis* sp., *Sitobion* sp., *Trialeurodes vaporariorum, Trioza erytreae* and *Unaspis citri*; (k) Hymenoptera, for example, *Acromyrmex, Atta* sp., *Cephus* sp., *Diprion* sp., Diprionidae, *Gilpinia polytoma, Hoplocampa* sp., *Lasius* sp., *Monomorium pharaonis, Neodiprion* sp., *Solenopsis* sp. and *Vespa* sp.; (l) Diptera, for example, *Aedes* sp., *Antherigona soccata, Bibio hortulanus, Calliphora erythrocephala, Ceratitis* sp., *Chrysomyia* sp., *Culex* sp., *Cuterebra* sp., *Dacus* sp., *Drosophila melanogaster, Fannia* sp., *Gastrophilus* sp., *Glossina* sp., *Hypoderma* sp., *Hyppobosca* sp., *Liriomyza* sp., *Lucilia* sp., *Melanagromyza* sp., *Musca* sp., *Oestrus* sp., *Orseolia* sp., *Oscinella frit, Pegomyia hyoscyami, Phorbia* sp., *Rhagoletis pomonella, Sciara* sp., *Stomoxys* sp., *Tabanus* sp., *Tannia* sp. and *Tipula* sp.; (m) Siphonaptera, for example, *Ceratophyllus* sp. and *Xenopsylla cheopis* and (n) from the order Thysanura, for example, *Lepisma saccharina*. The active ingredients according to the invention may further be used for controlling crucifer flea beetles (*Phyllotreta* sp.), root maggots (*Delia* sp.), cabbage seedpod weevil (*Ceutorhynchus* sp.) and aphids in oil seed crops such as canola (rape), mustard seed, and hybrids thereof, and also rice and maize. Sarmentine and/or its analogs in these materials can be the only active ingredient(s) or a mixture with any other phytopathogenic and/or herbicidal compounds. In some embodiments, non-limiting examples of natural herbicides that can used with sarmentine and its analogs include but are not limited to catechin, ellagic acid, sorgoleone, juglone, ceratiolin, usnic acid, 1,8-cineole, geranial, neral, cinmethylin, solstitiolide, ailanthone, chaparrine, ailanthinol B, hydroxamic acids, glucohirsutin, hirsutin, arabin, meta-tyrosine. Percent of sarmentine and/or its analogs in these compositions can be within a range of 0.01% to 99.99%.

In other embodiments, non-limiting examples of synthetic herbicides that can used with sarmentine and/or its analog include but are not limited to aryloxyphenoxypropionic herbicides (e.g., chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop); benzoic acid herbicides (e.g., chloramben, dicamba, 2,3,6-TBA and tricamba); benzofuranyl alkylsulfonate herbicides (e.g., benfuresate and ethofumesate); benzoylcyclohexanedione herbicides (e.g., mesotrione, sulcotrione, tefuryltrione and tembotrione); carbamate herbicides (e.g., asulam, carboxazole chlorprocarb, dichlormate, fenasulam, karbutilate and terbucarb); carbanilate herbicides (e.g., barban, BCPC, carbasulam, carbetamide, CEPC, chlorbufam, chlorpropham, CPPC, desmedipham, phenisopham, phenmedipham, phenmedipham-ethyl, propham); cyclohexene oxime herbicides (e.g., alloxydim, butroxydim, clethodim, cloproxydim, cycloxydim, profoxydim, sethoxydim, tepraloxydim and tralkoxydim); cyclopropylisoxazole herbicides (e.g., isoxachlortole and isoxaflutole); dicarboximide herbicides (e.g., benzfendizone, cinidon-ethyl, flumezin, flumiclorac, flumioxazin and flumipropyn); dinitroaniline herbicides (e.g., benfluralin, butralin, dinitramine, ethalfluralin, fluchloralin, isopropalin, methalpropalin, nitralin, oryzalin, pendimethalin, prodiamine, profluralin and trifluralin); dinitrophenol herbicides (e.g., dinofenate, dinoprop, dinosam, dinoseb, dinoterb, DNOC, etinofen and medinoterb); dithiocarbamate herbicides (e.g., dazomet and metam; halogenated aliphatic herbicides such as alorac, chloropon, dalapon, flupropanate, hexachloroacetone, iodomethane, methyl bromide, monochloroacetic acid, SMA and TCA); imidazolinone herbicides (e.g., imazamethabenz, imazamox, imazapic, imazapyr, imazaquin and imazethapyr); inorganic herbicides (e.g., ammonium sulfamate, borax, calcium chlorate, copper sulfate, ferrous sulfate, potassium azide, potassium cyanate, sodium azide, sodium chlorate and sulfuric acid); nitrophenyl ether herbicides (e.g., acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen); nitrile herbicides (e.g., bromobonil, bromoxynil, chloroxynil, dichlobenil, iodobonil, ioxynil and pyraclonil); organophosphorus herbicides (e.g., amiprofos-methyl, anilofos, bensulide, bilanafos, butamifos, 2,4-DEP, DMPA, EBEP, fosamine, glufosinate, glyphosate and piperophos); phenoxy herbicides (e.g., bromofenoxim, clomeprop, 2,4-DEB, 2,4-DEP, difenopenten, disul, erbon, etnipromid, fenteracol and trifopsime); phenoxyacetic herbicides (e.g., 4-CPA, 2,4-D, 3,4-DA, MCPA, MCPA-thioethyl and 2,4,5-T); phenoxybutyric herbicides (e.g., 4-CPB, 2,4-DB, 3,4-DB, MCPB and 2,4,5-TB); phenoxypropionic herbicides (e.g., cloprop, 4-CPP, dichlorprop, dichlorprop-P, 3,4-DP, fenoprop, mecoprop and mecoprop-P); phenylenediamine herbicides (e.g., dinitramine and prodiamine); picolinic acid herbicides (e.g., aminopyralid, clopyralid and picloram); pyrazolyl herbicides (e.g., benzofenap, pyrazolynate, pyrasulfotole, pyrazoxyfen, pyroxasulfone and topramezone); pyrazolylphenyl herbicides (e.g., fluazolate and pyraflufen; pyridazine herbicides such as credazine, pyridafol and pyridate); pyridazinone herbicides (e.g., brompyrazon, chloridazon, dimidazon, flufenpyr, metflurazon, norflurazon, oxapyrazon and pydanon); pyridine herbicides (e.g., cliodinate, dithiopyr, fluroxypyr, haloxydine, picolinafen, pyriclor, thiazopyr and triclopyr); pyrimidinediamine herbicides (e.g., iprymidam and tioclorim); quaternary ammonium herbicides (e.g., cyperquat, diethamquat, difenzoquat, diquat, morfamquat and paraquat); pyrimidinyloxybenzoic acid herbicides (e.g., bispyribac and pyriminobac); thiocarbamate herbicides (e.g., butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, triallate and vemolate); sulfonamide herbicides (e.g. asulam, carbasulam, fenasulam, oryzalin, penoxsulam, pyroxsulam); triazine herbicides (e.g., dipropetryn, triaziflam and trihydroxytriazine, atrazine, chlorazine, cyanazine, cyprazine, eglinazine, ipazine, mesoprazine, procyazine, proglinazine, propazine, sebuthylazine, simazine, terbuthylazine and trietazine, atraton, methometon, prometon, secbumeton, simeton and terbumeton; ametryn, aziprotryne, cyanatryn, desmetryn, dimethametryn, methoprotryne, prometryn, simetryn and terbutryn); triazinone herbicides (e.g., ametridione, amibuzin, hexazinone, isomethiozin, metamitron and metribuzin); triazolopyrimidine herbicides (chloransulam, diclosulam, florasulam, flumetsulam, metosulam); urea herbicides (e.g., benzthiazuron, cumyluron, cycluron, dichloralurea, diflufenzopyr, isonoruron, isouron, methabenzthiazuron, monisouron and noruron; anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; chlorsulfuron, cinosulfuron, ethametsulfuron, iodosulfuron, metsulfuron, prosulfuron, thifensulfuron, triasulfuron, tribenuron, triflusulfuron and tritosulfuron; buthiuron, ethidimuron, tebuthiuron, thiazafluron and thidiazuron), etc.

The composition may further comprise an additional fungicidal agent such as myclobutanil, and fenhexamide, azoxystrobin, azoxystrobin combination, boscalid, *bacillus subtilis*, copper sulfate, chlorothalonil, copper hydroxide, cymoxanil, dimethomorph, dechloropropene, fosetyl-aluminum, fludioxonil, fenamidone, iprodione, mefenoxam, mancozeb, metalaxyl, metam sodium, potassium bicarbonate, pyraclostrobin, propiconazole, propicocarb, thiram, thiabendazole, thiophanate-methyl, trifloxystrobin, vinclozolin, sulfur, ziram. They also include the following antibacterial agents such as streptomycin and oxytetracycline.

The composition and method of the present invention will be further illustrated in the following, non-limiting examples. The examples are illustrative of various embodiments only and do not limit the claimed invention regarding the materials, conditions, weight ratios, process parameters and the like recited herein.

EXAMPLE

In the instant Example, results are disclosed showing that the methanol extract of dry long pepper (*Piper longum* L.) fruits are phytotoxic against bib lettuce (*Lactuca sativa*, L.) seedlings. The extract was subjected to bioassay-guided isolation and yielded one active compound. The active compound was identified as a known compound, called sarmentine and is the first time it is isolated from *P. longum*. Phytotoxic activity of sarmentine was examined with a variety of seedlings from crops, sedge and weeds. Results indicated that sarmentine is a contact herbicide and possesses broad-spectrum herbicidal activity. Sarmentine in the different dried *P. longum* fruits was quantified by liquid chromatography-mass spectrometry and found to vary dramatically, ranging from almost zero to 0.57%. In addition, a series of sarmentine analogs were then synthesized to study the structure-activity relationship (SAR). Results from SAR study suggested that either the long unsaturated fatty acid (i.e., 2E,4E-decandienoic acid) or the amine (i.e., pyrrolidine) was crucial for activity, but the amide bond with a secondary amine seemed to be necessary for the phytotoxic activity of sarmentine.

MATERIALS AND METHODS

Chemical:

Sepra C18-E (50 μM and 60 Å) and Silica gel sorbent (70-230 mesh size) were purchased from Phenomenex® (Torrance, Calif., USA) and Fisher Scientific (Fair Lawn, N.J., USA), respectively. Polyoxyethylene (20) Sorbitan Monolaurate (i.e., Glycosperse O-20 KFG) and sodium lauryl sulfate (i.e., SLS) were obtained as free samples from Lonza Inc. (Allendale, N.J., USA) and Spectrum Chemical Mfg. Corp. (New Brunswick, N.J., USA), respectively. Cyclopentylamine, trans-cinnamic acid, ethyl trans-2-cis-4-decadienoate, hexamethyleneimine, trans-2-decenoic acid, decanoic acid, 4-dimethylaminopyridine are purchased from ACROS Organics (Morris Plains, N.J., USA). All other chemicals were of reagent grades.

Fruits of *P. longum* and Pre-Treatment:

Four samples of dried *P. longum* fruits were purchased from Chinese medicinal herb stores. The fruits were completely ground with a coffee grinder (Toastmaster Inc., Boonville, Mich., USA). The freshly ground powder of fruits was extracted with appropriate solvents.

Weed, Sedge and Crop Seedlings:

All weed, sedge and crop seedlings were planted in 8 cm×8 cm×7.2 cm or 10 cm×10 cm×9 cm plastic pots. Seedlings including pigweed (*Amaranthus retroflexus*, L.), barnyard grass (*Echinochloa crusgalli* L.), bindweed (*Convolvulus arvensis* L.), crabgrass (*Digitaria sanguinalis* L.), dandelion (*Taraxacum officinale* F.), lambsquarters (*Chenopodium album* L.), bluegrass (*Poa annua* L.), wild mustard (*Brassica kaber* L.), black nightshade (*Solanum nigrum* L.), curly dock (*Rumex crispus* L.), horseweed (*Conyza Canadensis* L.), sweet corn (*Zea may* S.) and wheat PR 1404 (*Triticum aestivum* L.) were planted in Super Soil potting soil. Seedlings including rice M-104 (*Oryza sativa* L.), sedge (*Cyperus difformis* L.) and sprangletop (*Leptochloa fascicularis* Lam) were planted in mud which was collected from rice field (Woodland, Calif., USA). When treated, all seedlings were 15 days old except for rice (10 days), wheat (20 days), corn (20 days) sprangletop (20 days old), sedge (20 days old) and horseweed (70 days old).

Bioassay-Guided Extraction and Isolation:

The active compound was isolated by four major steps described as follows: 1) the methanol extract of freshly ground *P. longum* fruit powder was screened in a 96-well plate bioassay with bib lettuce (*Lactuca sativa*) seedlings; 2) the methanol extract (0.5 gram) was subjected to a reverse C-18 column and was eluted with 20%, 40%, 60%, 80% and 100% methanol in water; Fractions were dried under vacuum and efficacy was re-evaluated by 96-well plate bioassay with bib lettuce (*Lactuca sativa*) seedlings. The active fraction was used to guide next step for separation; 3) Ethyl acetate extract (17.6 g) was loaded into a flash column. The column was sequentially eluted with hexane (1 L), hexane/ethyl acetate (3:1, 1 L), hexane/ethyl acetate (1:1, 1 L), ethyl acetate (1 L) and acetone (1 L). Based on thin layer chromatography (TLC), nine fractions were collected. The efficacy of each fraction was evaluated by foliar spraying of barnyard grass (*Echinochloa crusgalli*). The concentration of each fraction was 5 mg/mL with a carrier solution consisting of 4% ethanol and 0.2% glycosperse O-20 KFG. The active fractions (3.4 g) were combined together and subjected to the next step; 4) A secondary silica column was performed with a combination of hexane and ethyl acetate (3:1) as an elution solvent. The active ingredient (0.96 g) was re-crystallized at −20° C. in a mixture of hexane and ethyl acetate and yielded a pure active compound. Purity was examined by liquid chromatography and mass spectrometry (LC/MS). Detailed conditions for LC/MS was described later in Materials and Methods.

Structural Elucidation:

Structural identification of the active compound was based on data from both Nuclear Magnetic Resonance (NMR) spectra and high resolution mass spectrometry. NMR spectra including $^1$H, $^{13}$C, DEPT, COSY, HMQC and HMBC were acquired from a Bruker Avance 600 spectrometer (Bruker BioSpin Corporation, Billerica, Mass., USA). Chemical shift values are given in ppm downfield from an internal standard (trimethylsilane). Signal multiplicities are represented as singlet (s), doublet (d), double doublet (dd), triplet (t), quartet (q), quintet (quint) and multiplet (m). Exact mass of the active compound was determined by high-performance liquid chromatography—tandem mass spectroscopy Comparison of the Active Compound from Different Fruit Samples:

Ground fruit powder (10 g) of different samples was soaked in ethyl acetate (50 mL) for 20 h at room temperature. The solution was filtered by a Whatman® qualitative filter paper (NO 1, Ø 155 mm). The residue and filter paper was washed by ethyl acetate (25 mL). The combined organic phase was dried under vacuum. The weight of each extract was recorded. The active compound in the extracts was quantified by LC/MS.

Quantification of the Active Compound in the Ethyl Acetate Extract of Dried Fruits by (LC/MS):

Chromatographic separation was performed at 25° C. on a Thermo high performance liquid chromatography (HPLC) instrument equipped with Finnigan Surveyor PDA plus detector, autosampler plus, MS pump and a 4.6 mm×100 mm Luna C18 5 µm column (Thermo Electron Corp., San Jose, Calif.). The solvent system consisted of water (solvent A) and acetonitrile (solvent B). The mobile phase began at 10% solvent B and was linearly increased to 100% solvent B over 20 min and then kept for 4 min, and finally returned to 10% solvent B over 3 min and kept for 3 min. The flow rate was 0.5 mL/min. The injection volume was 10 µL and the samples were kept at room temperature in an auto sampler. The active compound was detected by a positive electrospray ionization mode in a full scan mode (m/z 100-1500 Da) on a LCQ DECA XP$^{plus}$ Mass Spectrometer (Thermo Electron Corp., San Jose, Calif.). The flow rate of the nitrogen gas was fixed at 30 and 15 arb for the sheath and aux/sweep gas flow rate, respectively. Electrospray ionization (ESI) was performed with a spray voltage set at 5000 V and a capillary voltage at 35.0 V. The capillary temperature was set at 400° C.

The standard of the active compound was obtained by repeated crystallization in laboratory. A series of standard concentrations (125, 62.5, 31.25, 15.6, 7.8, 3.9, 1.95 and 0.976 ng/ml) was made in ethanol. Three independent samples (2.5 µg/mL in ethanol) for each extract were made. Mass spectra were run in a SIM mode with a mass range of 221.0-224.0 and retention time (16.94 min). The limits of detection (LOD) of the active compound were determined by running decreasing amounts of standard solution until the ratio of the signal of the active compound over the background was greater or equal to 3. The concentration of fruit samples was presented by an average of three independent samples with a standard deviation.

Synthesis of Sarmentine Analogs:

To the ice-cooled carboxylic acid (3 mmole) solution in dichloromethane (20 ml) was sequentially added 1-ethyl-3-(3'-dimethylaminopropyl) carbodiimide (3.3 mmole) and 4-dimethylaminopyridine (3 mmole). After 5 min, amine (3.3 mmole) was added in the reaction solution. The reaction was slowly warmed to the room temperature and lasted overnight. The reaction was extracted with ethyl acetate (200 mL). The organic phase was dried with anhydrous sodium sulfate. After evaporation under vacuum, the residue was run through a silica gel column with an appropriate ratio of ethyl acetate in hexane. The yield of the final products ranged from 85% to 90%. The final products were characterized with proton NMR.

N-Cyclopentylcinnamamide (7)

$^1$H NMR (CDCl$_3$): δ (ppm) 7.62 (d, J=15.6 Hz, 1H), 7.50 (d, J=7.0 Hz, 2H), 7.35 (m, 3H), 6.37 (d, J=15.6, 1H), 5.61 (d, J=5.0, Hz, 1H, NH), 4.35 (sextet, J=7.0, 1H), 2.06 (m, 2H), 1.71 (m, 2H), 1.64 (m, 2H), 1.46 (m, 2H).

N-(trans-Cinnamoyl)pyrrolidine (11)

$^1$H NMR (CDCl$_3$): δ (ppm) 7.70 (d, J=15.5 Hz, 1H), 7.53 (d, J=7.0 Hz, 2H), 7.36 (m, 3H), 6.74 (d, J=15.5, 1H), 3.63 (t, J=7.0, 2H), 3.60 (t, J=7.0, 2H), 2.01 (quintet, J=7.0, 2H), 1.91 (quintet, J=7.0, 2H).

N-(trans-Cinnamoyl)piperidine (15)

$^1$H NMR (CDCl$_3$): δ (ppm) 7.64 (d, J=15.5 Hz, 1H), 7.52 (d, J=7.2 Hz, 2H), 7.36 (m, 3H), 6.90 (d, J=15.5, 1H), 3.67 (s, 2H), 3.59 (s, 2H), 1.68 (m, 2H), 1.62 (m, 4H).

N-(trans-Cinnamoyl) hexamthleneimine (19)

$^1$H NMR (CDCl$_3$): δ (ppm) 7.70 (d, J=15.4 Hz, 1H), 7.52 (d, J=7.6 Hz, 2H), 7.36 (m, 3H), 6.88 (d, J=15.4, 1H), 3.63 (t, J=6.0, 2H), 3.61 (t, J=6.0, 2H), 1.76 (m, 4H), 1.59 (m, 4H).

N-Cyclopentyldecanamide (4)

$^1$H NMR (CDCl$_3$): δ (ppm) 5.35 (br, 1H), 4.22 (sextet, J=7.00, 1H), 2.12 (t, J=7.20, 2H), 1.98 (m, 2H), 1.59-1.67 (m, 6H), 1.26-1.36 (m, 14H), 0.88 (t, J=7.00, 3H).

N-(Decanoyl)pyrrolidine (8)

$^1$H NMR (CDCl$_3$): δ (ppm) 3.45 (t, J=6.80, 2H), 3.40 (t, J=6.80, 2H), 2.24 (t, J=7.20, 2H), 1.94 (quintet, J=6.80, 2H), 1.84 (quintet, J=6.80, 2H), 1.62 (quintet, J=7.20, 2H), 1.25-1.30 (m, 12H), 0.87 (t, J=7.20, 3H).

N-(Decanoyl)piperidine (12)

$^1$H NMR (CDCl$_3$): δ (ppm) 3.55 (t, J=5.20, 2H), 3.39 (t, J=5.20, 2H), 2.31 (t, J=7.60, 2H), 1.58-1.65 (m, 4H), 1.52-1.57 (m, 4H), 1.20-1.30 (m, 12H), 0.87 (t, J=7.20, 3H).

N-(Decanoyl)hexamethyleneimine (16)

$^1$H NMR (CDCl$_3$): δ (ppm) 3.52 (t, J=6.00, 2H), 3.42 (t, J=6.00, 2H), 2.30 (t, J=7.80, 2H), 1.66-1.74 (m, 4H), 1.60-1.66 (m, 2H), 1.50-1.6.0 (m, 4H), 1.20-1.30 (m, 12H), 0.87 (t, J=7.20, 3H).

N-Cyclopentyldecanamide (5)

$^1$H NMR (CDCl$_3$): δ (ppm) 6.82 (dt, J$_1$=15.20, J$_2$=7.20, 1H), 5.71 (d, J=15.20, 1H), 5.33 (br, 1H), 4.27 (sextet, J=7.00, 1H), 2.15 (m, 2H), 2.10 (m, 2H), 1.67 (m, 2H), 1.60 (m, 2H), 1.40 (m, 4H), 1.28 (m, 8H), 0.88 (t, J=7.00, 3H).

N-(Decenoyl)pyrrolidine (9)

$^1$H NMR (CDCl$_3$): δ (ppm) 6.90 (dt, J$_1$=15.20, J$_2$=7.00, 1H), 6.07 (d, J=15.20, 1H), 3.52 (t, J=6.30, 2H), 3.50 (t, J=6.30, 2H), 2.19 (m, 2H), 1.96 (quintet, J=7.00, 2H), 1.85 (quintet, J=7.00, 2H), 1.44 (m, 2H), 1.28 (m, 8H), 0.88 (t, J=7.00, 3H).

N-(Decenoyl)piperidine (13)

$^1$H NMR (CDCl$_3$): δ (ppm) 6.82 (dt, J$_1$=15.20, J$_2$=7.00, 1H), 6.23 (d, J=15.20, 1H), 3.59 (t, J=6.30, 2H), 3.47 (t, J=6.30, 2H), 2.17 (m, 2H), 1.64 (quintet, J=5.60, 2H), 1.56 (quintet, J=5.60, 4H), 1.44 (quintet, J=7.00, 2H), 1.28 (m, 8H), 0.88 (t, J=7.00, 3H).

N-(Decenoyl)hexamethyleneimine (17)

$^1$H NMR (CDCl$_3$): δ (ppm) 6.91 (dt, J$_1$=15.20, J$_2$=7.00, 1H), 6.21 (d, J=15.20, 1H), 3.57 (t, J=6.00, 2H), 3.49 (t, J=6.00, 2H), 2.17 (m, 2H), 1.73 (m, 4H), 1.56 (m, 4H), 1.45 (m, 2H), 1.28 (m, 8H), 0.88 (t, J=7.00, 3H).

N-Cyclopentyl 2E,4Z-decadienamide (6)

$^1$H NMR (CDCl$_3$): δ (ppm) 7.55 (dd, J$_1$=14.80, J$_2$=11.70, 1H), 6.06 (t, J=11.70, 1H), 5.79 (d, J$_1$=14.80, 1H), 5.75 (m, 1H), 5.50 (br, 1H), 4.30 (sextet, J=7.00, 1H), 2.29 (quartet, J=8.20, 2H), 2.01 (m, 2H), 1.68 (m, 2H), 1.61 (m, 2H), 1.40 (m, 2H), 1.28 (m, 6H), 0.88 (t, J=7.00, 3H).

(2E,4Z-Decadienoyl)pyrrolidine (10)

$^1$H NMR (CDCl$_3$): δ (ppm) 7.62 (dd, J$_1$=14.60, J$_2$=11.70, 1H), 6.17 (d, J=14.60, 1H), 6.13 (t, J=11.70, 1H), 5.78 (m, 1H), 3.55 (t, J=7.00, 2H), 3.52 (t, J=7.00, 2H), 2.30 (quartet, J=7.40, 2H), 1.97 (quintet, J=7.40, 2H), 1.87 (quintet, J=7.40, 2H), 1.40 (quintet, J=7.40, 2H), 1.29 (m, 4H), 0.88 (t, J=7.00, 3H).

(2E,4Z-Decadienoyl)piperidine (14)

$^1$H NMR (CDCl$_3$): δ (ppm) 7.59 (dd, J$_1$=14.60, J$_2$=11.70, 1H), 6.34 (d, J=14.60, 1H), 6.13 (t, J=11.70, 1H), 5.78 (m, 1H), 3.62 (t, J=7.00, 2H), 3.45 (t, J=7.00, 2H), 2.31 (quartet, J=7.40, 2H), 1.67 (quintet, J=7.40, 4H), 1.57 (quintet, J=7.40, 2H), 1.40 (m, 2H), 1.27 (m, 4H), 0.88 (t, J=7.00, 3H).

(2E,4Z-Decadienoyl)hexamethleneimine (18)

$^1$H NMR (CDCl$_3$): δ (ppm) 7.64 (dd, J$_1$=14.60, J$_2$=11.70, 1H), 6.30 (d, J=14.60, 1H), 6.16 (t, J=11.70, 1H), 5.78 (m, 1H), 3.60 (t, J=7.00, 2H), 3.51 (t, J=7.00, 2H), 2.31 (quartet, J=7.40, 2H), 1.76 (m, 4H), 1.57 (m, 4H), 1.40 (m, 2H), 1.30 (m, 4H), 0.88 (t, J=7.00, 3H).

Evaluation of Herbicidal Activity:

Herbicidal activity of the active compound and synthesized compounds was evaluated by foliar spraying. Spraying carrier solution contained 2% ethanol, 0.2% glycosperse O-20 and 0.1% sodium lauryl sulfate. Freshly made solution with the evaluated compound at a concentration of 5 mg/mL was used. In the spectrum study, spraying volume was dependent on the foliar surface area, ranging from approximately 1 to 3 mL/pot plants. One or two pots of plants were treated for each. Number of pots was dependent on both foliar area and availability. In the structure-activity relationship study, one pot of barnyard grass was used and the spraying volume of each compound was 3 mL of 5 mg/mL. Phytotoxic activity was evaluated at least 3 days after spraying. Efficacy of phytotoxic activity was graded as I (no effect), II (<20%), III (20-40%), IV (40-60%), V (60-80%) and VI (80-100%).

RESULTS

Bio-Assay Guided Purification:

The active compound was obtained by the following procedures. Initial experiment indicated phytotoxic activity in the methanol extract of P. longum dried fruits. The active ingredient(s) existed in the fraction with 100% methanol elution when a reversed C18 column was used, and no phytotoxic activity was shown from other fractions at 5 mg/mL (not shown). In our next experiment, ethyl acetate extract was run though a flash silica column. The elution was collected as 9 fractions (based on TLC indication). The weight of each fraction from 1 to 9 was 3.0, 1.0, 1.7, 3.6, 0.9, 2.5, 1.2, 0.2 and 2.3 gram, respectively. Two out of nine fractions were active against barnyard grass (FIG. 1). The combined two active fractions (i.e., Fr 5 & Fr 6, 3.4 g) were re-run through a silica column and yielded slightly yellowish oil as the active compound. This oil was re-crystallized in a mixture of hexane and ethyl acetate at −20° C. and obtained as colorless oil (0.83) at room temperature.

Structure Elucidation:

The active compound was identified based on the following evidence: High resolution mass data (TOF MS ESI$^+$) is 222.5386, indicating that the molecular formula of the active compound is most possibly $C_{14}H_{23}NO$. The data from $^1$H and $^{13}$C NMR listed in the Table 1 further supported this molecular formula. Data in the proton NMR indicate that there are a total of 23 protons including 4-olefenic protons (4CH), 1CH$_3$ and 8CH$_2$. Data from $^{13}$C NMR and DEPT-135 (not shown) confirmed that there are 14 carbons including 1 amide carbonyl (N—CO—), 4CH, 8CH$_2$ and 1CH$_3$. Data from COSY (not shown) indicated that 2 spin systems are present in the molecule. One contains 4 consecutive CH$_2$. And another contains 4 conjugated olefin protons which are further connected to CH$_2$CH$_2$CH$_2$CH$_3$. Moreover, data from HMBC (not shown) indicated that the above-mentioned 2-spin systems are connected through an amide carbonyl to give the plane structure. Finally, geometric conformation is trans for both double bonds based on coupling constants (J=14.4 Hz). This active compound (Table 1) is a known compound called sarmentine, which was first purified from dried P. sarmentosum fruit powder (Likhitwitayawuid, K., Ruangrungsi, N, Lange, G and Decicco, C., Structural Elucidation and Synthesis of New Components isolated from Piper Samentosum, Tetrahedron 1987 (43) 3689-3694) and also from P. nigrum (Kiuchi, F.; Nakamura, N.; Tsuda, Y.; Kondo, K.; Yoshimura, H. Studies on crude drugs effective on visceral larva migrans, IV isolation and identification of larvicidal principles in Pepper, Chem Pharm. Bull, 1988, 36, 2452-2465). However, it is the first time that it was isolated from P. longum and found to be a phytotoxic compound.

TABLE 1

<sup>1</sup>H and <sup>13</sup>C NMR (CDCl$_3$) data of sarmentine

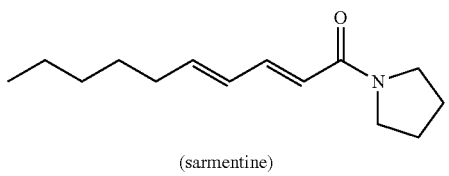 [SMILES: CCCCC/C=C/C=C/C(=O)N1CCCC1]

| NO | $^{13}$C NMR data | $^{1}$H NMR data |
|---|---|---|
| 1 | 165.4 | — |
| 2 | 120.0 | 6.08 1H d (J = 14.4 Hz) |
| 3 | 142.4 | 7.26 1H dd (J$_1$ = 14.4, J$_2$ = 10.8 Hz) |
| 4 | 128.8 | 6.16 1H dd (J$_1$ = 10.8, J$_2$ = 9.6 Hz) |
| 5 | 143.4 | 6.07 1H dt (J$_1$ =14.4, J$_2$ = 7.2 Hz) |
| 6 | 33.1 | 2.13 2H quartet (J = 7.2 Hz) |
| 7 | 26.3 | 1.39 2H quintet (J = 7.2 Hz) |
| 8 | 24.5 | 1.27 2H m |
| 9 | 22.7 | 1.27 2H m |
| 10 | 14.2 | 0.87 3H t (J = 7.2 Hz) |
| 1' | 46.6 | 3.50 2H t (J = 7.2 Hz) |
| 2' | 31.5 | 1.95 2H quintet (J = 7.2 Hz) |
| 3' | 28.6 | 1.85 2H quintet (J = 7.2 Hz) |
| 4' | 46.0 | 3.52 2H t (J = 7.2 Hz) |

Herbicidal Spectrum of Sarmentine:

Phytotoxic activity of sarmentine depended on the concentration. The optimal concentration of sarmentine was 5 mg/mL for excellent control of barnyard grass (FIG. 2). Therefore, such a concentration was subjected to herbicidal spectrum study. Due to the hydrophobic property of sarmentine, a carrier solution containing 0.2% glycosperse O-20, 2% ethanol and 0.1% sodium lauryl sulfate was used. Although this solution contains a high concentration of surfactants, sarmentine can stay suspended in this solution no more than 15 min. Therefore, sarmentine was made freshly just before spraying. In addition, this solution did not show any phytotoxic activity toward tested plants when results were recorded.

Sarmentine displayed phytotoxic activity against a variety of plants including sedge, crops and weeds (Table 2).

TABLE 2

Phytoxtoxic activity of sarmentine toward different plants

| No | Plant name | Efficacy* |
|---|---|---|
| 1 | Pigweed (*Amaranthus retroflexus*, L.) | VI |
| 2 | Barnyard grass (*Echinochloa crusgalli* L.) | VI |
| 3 | Bindweed (*Convolvulus arvensis*, L.) | VI |
| 4 | Crabgrass (*Digitaria sanguinalis* L.) | VI |
| 5 | Horse weed (*Conyza Canadensis* L.) | II |
| 6 | Sedge (*Cyperus difformis* L.) | III |
| 7 | Sprangletop (*Leptochloa fascicularis* Lam.) | VI |
| 8 | Dandelion (*Taraxacum officinale* F.) | VI |
| 9 | Lambsquarters (*Chenopodium album* L.) | VI |
| 10 | Bluegrass (*Poa annua* L.) | VI |
| 11 | Wild mustard (*Brassica kaber* L.) | VI |
| 12 | Black nightshade (*Solanum nigrum* L.) | VI |
| 13 | Curly dock (*Rumex crispus* L.) | VI |
| 14 | Sweet corn (*Zea mays* S.) | VI |
| 15 | Wheat (PR 1404) (*Triticum aestivum* L.) | VI |
| 16 | Rice (M 104) (*Oryza saliva* L) | I |

*Efficacy of phytotoxic activity was graded as I (no effect), II (<20%), III (20-40%), IV (40-60%), V (60-80%) and VI (80-100%).

Phytotoxic activity of sarmentine was dependent on the plants, ranging from zero to 100% killing. No visible phytotoxic activity (after 10 days) was shown on rice plants toward sarmentine. Slightly phytotoxic activity of sarmentine toward sedge and horseweed was shown. However, highly phytotoxic activity of sarmentine was displayed toward pigweed, barnyard grass, bindweed, crabgrass, sprangletop, dandelion, lambsquarters, blue grass, wild mustard, black nightshade, curly dock, sweet corn and wheat. The phytotoxic activity may be related to age of plants. For example, horseweed (70-day-old) was much older than other weeds, but less phytotoxic activity was shown.

Structure-Activity Relationship (SAR):

The SAR study suggested that either the long unsaturated fatty acid or pyrrolidine of sarmentine is crucial for phytotoxic activity, but the amide bond with a secondary amine seemed to be necessary. This conclusion was supported by the following experimental results which are summarized below in Table 3.

TABLE 3

Phytotoxic activity of sarmentine and its analogs toward barnyard grass

| No | Structures | Efficacy* |
|---|---|---|
| 1 | vector | I |
| 2 | 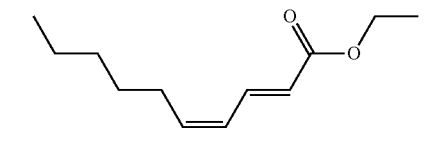 (sarmentine) | VI |
| 3 | 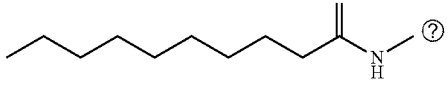 | II |
| 4 | 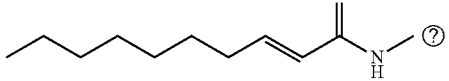 | II |
| 5 | 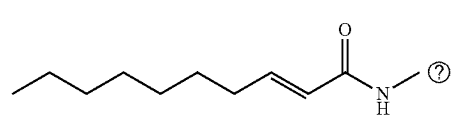 | II |

TABLE 3-continued

Phytotoxic activity of sarmentine and its analogs toward barnyard grass

| No | Structures | Efficacy* |
|----|------------|-----------|
| 6  | 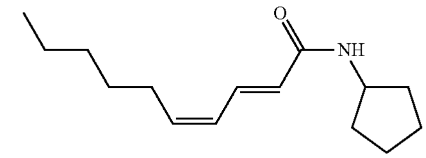 [SMILES: CCCCC/C=C\C=C\C(=O)NC1CCCC1]           | II        |
| 7  | 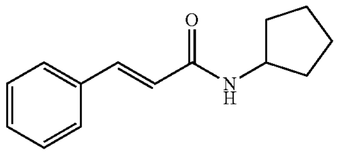 [SMILES: O=C(/C=C/c1ccccc1)NC1CCCC1]           | II        |
| 8  | 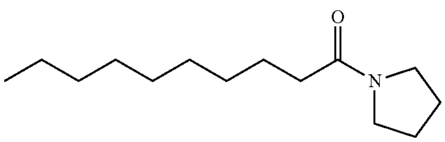 [SMILES: CCCCCCCCCC(=O)N1CCCC1]           | VI        |
| 9  | 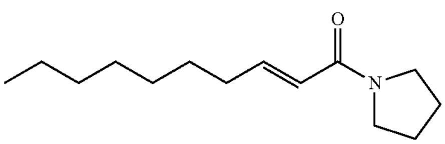 [SMILES: CCCCCCC/C=C/C(=O)N1CCCC1]           | VI        |
| 10 | 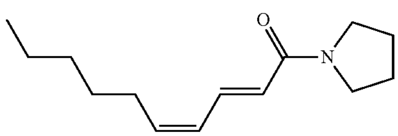 [SMILES: CCCCC/C=C\C=C\C(=O)N1CCCC1]           | VI        |
| 11 | 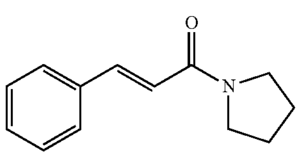 [SMILES: O=C(/C=C/c1ccccc1)N1CCCC1]           | VI        |
| 12 | 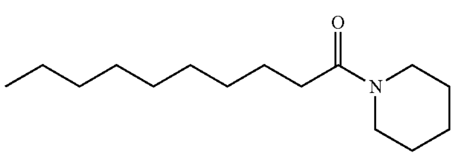 [SMILES: CCCCCCCCCC(=O)N1CCCCC1]           | VI        |
| 13 | 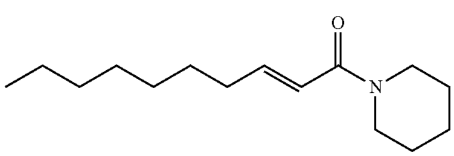 [SMILES: CCCCCCC/C=C/C(=O)N1CCCCC1]           | VI        |
| 14 | 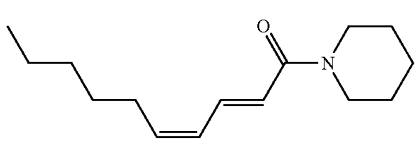 [SMILES: CCCCC/C=C\C=C\C(=O)N1CCCCC1]           | VI        |
| 15 | 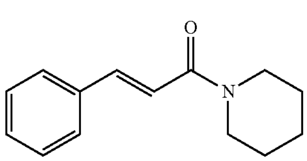 [SMILES: O=C(/C=C/c1ccccc1)N1CCCCC1]           | IV        |
| 16 | 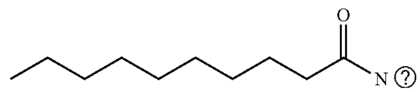           | VI        |
| 17 | 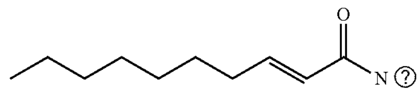           | VI        |
| 18 | 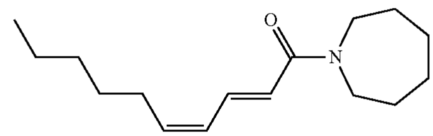 [SMILES: CCCCC/C=C\C=C\C(=O)N1CCCCCC1]           | VI        |
| 19 | 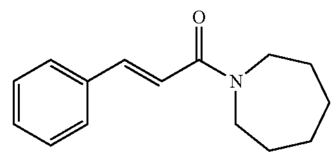 [SMILES: O=C(/C=C/c1ccccc1)N1CCCCCC1]           | II        |
| 20 | 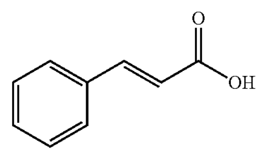 [SMILES: O=C(O)/C=C/c1ccccc1]           | V         |
| 21 | 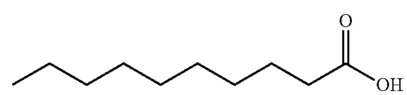           | VI        |
| 22 | 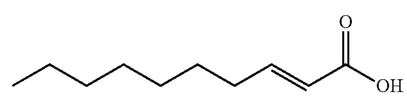           | VI        |
| 23 | 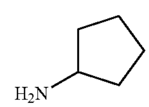           | I         |
| 24 | 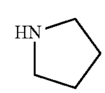           | I         |
| 25 | 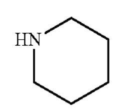           | I         |
| 26 | 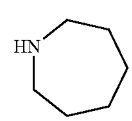           | I         |

*Efficacy of phytotoxic activity was graded as I (no effect), II (<20%), III (20-40%), IV (40-60%), V (60-80%) and VI (80-100%).

Phytotoxic activity remained the same as the acid moiety of sarmentine was replaced by structurally similar fatty acids such as 2E,4Z-decandienoic acid (i.e., geometric isomer of 2E, 4E-decandienoic acid) with two double bonds (10), 2 E-decenoic acid with one double bond (9) and decanoic acid without any double bond (8), and even structurally different acid such as trans-cinnamic acid (11). This suggested that the acid moiety of sarmentine can be various acids when the amine is pyrrolidine. Similarly, when the acid moiety remained the same, the amine can be various. For example, phytotoxic activity remained the same in terms of decanoic acid when the amine was changed from a five member ring (8) to a six or seven member ring (12 & 16, respectively). However, phytotoxic activity dropped dramatically when the amide bond with a secondary amine was changed into an ester bond (e.g., 3) and an amide bond with a primary amine (e.g., 4-7). In addition, results from SAR study (Table 3) also indicated that the amine moiety of sarmentine, pyrrolidine (24), and its analogs such as cyclopentylamine (23), hexamethyleneimine (26) and piperidine (25) were non toxic to barnyard grass; but the analogs of the acid moiety of sarmentine such as decanoic acid (21), 2E-decenoic acid and (22) and trans-cinnamic acid (20) were very active. To obtain a better SAR, the length of carbon chain in the acid moiety and disubstituted amines (non ring system) should be further investigated.

Symptom of Phytotoxic Activity:

Sarmentine is a contact phytotoxic compound. When plants were treated with sarmentine solution, slightly black tiny spots would first show on the leaves and then became bigger and bigger until they covered the whole leaves, especially obvious on the barnyard grass. This symptom could be observed within half an hour to 2 hours after spraying. Predominant phytotoxic activity happened within 48 h after spraying. This symptom was observed very similarly to that of middle-chain fatty acids such as decanoic acid (21, Table 4) and 2E-decenoic acid (22, Table 3) during the SAR study.

Quantification of Sarmentine in Different *P. longum* Fruit Samples:

The standard curve of sarmentine (Y=83324X−30784, $R^2$=0.9998; X and Y stand for the concentration of sarmentine and peak area, respectively) was obtained. The limit of detection for sarmentine was 12 pg per injection (or 1.2 ng/mL). Based on this external standard curve, the concentration of sarmentine in the extracts of four different *P. longum* fruit samples varied from 0.0005% to 0.57%. These results are shown in Table 4.

TABLE 4

The concentration of sarmentine in different samples of dry *P. lungum* fruits

| Sample | Percent of sarmentine in the ethyl acetate extract | Extract weight (g) from 10 gram of ground dried fruit powder | Percent content of sarmentine in the dry fruit |
|---|---|---|---|
| 1 | 12.66 ± 0.45 | 0.45 ± 0.03 | 0.5697 ± .0380 |
| 2 | 1.83 ± 0.10 | 0.51 ± 0.03 | 0.0933 ± 0.0055 |
| 3 | 0.01 ± 0.001 | 0.55 ± 0.02 | 0.00055 ± 0.00002 |
| 4 | 0.008 ± 0.001 | 0.66 ± 0.03 | 0.00053 ± 0.00002 |

This difference in amounts of sarmentine present in each of the samples may result from the age and/or origin of the dried fruits. The quantity of sarmentine in the ground powder of dried *P. longum* fruits can be viewed by naked eyes because the higher the concentration of sarmentine is, the more oily the ground powder is. For example, no oil was visible for the ground powder of samples 3 and 4, but oily powder was seen in the ground powder from samples 1 and 2.

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

What is claimed is:

1. A method for modulating emergence of monocotyledonous, sedge or dicotyledonous weeds in a substrate in need thereof comprising applying to the weeds and/or the substrate an amount of a compound selected from the group consisting of N-(decenoyl)pyrrolidine, N-(trans-cinnamoyl)pyrrolidine, (2E,4Z-decadienoyl)pyrrolidine, N-(decenoyl)piperidine, (2E,4Z-decadienoyl)piperidine, (2E,4Z-decadienoyl)hexamethyleneimine, and N-(decenoyl)hexamethyleneimine effective to modulate emergence of monocotyledonous or dicotyledonous weeds in said substrate.

2. The method according to claim 1, wherein said weeds are broadleaved and/or grass weeds.

3. The method according to claim 1, wherein said substrate is soil, sediment, artificial growth substrates or water.

4. The method according to claim 1, wherein said weed is a rice weed.

5. The method according to claim 1, wherein said compound is applied to the substrate prior to emergence of said weed.

6. The method according to claim 1, wherein said compound is obtainable from a member of the *Piper* species in the Piperaceae family.

7. The method according to claim 1, wherein said method further comprises applying one or more other herbicidal agents.

* * * * *